(12) United States Patent
Nakamori

(10) Patent No.: US 8,597,690 B2
(45) Date of Patent: Dec. 3, 2013

(54) PHARMACEUTICAL COMPOSITION

(71) Applicant: Toshio Nakamori, Miyazaki (JP)

(72) Inventor: Toshio Nakamori, Miyazaki (JP)

(73) Assignee: Nakamori Pharmaceutical Co., Ltd., Miyazaki (JP)

( * ) Notice: Subject to any disclaimer, the term of this patent is extended or adjusted under 35 U.S.C. 154(b) by 0 days.

(21) Appl. No.: 13/623,522

(22) Filed: Sep. 20, 2012

(65) Prior Publication Data

US 2013/0084342 A1 Apr. 4, 2013

Related U.S. Application Data

(62) Division of application No. 12/735,557, filed as application No. PCT/JP2008/051276 on Jan. 29, 2008, now abandoned.

(51) Int. Cl.

| A61K 33/10 | (2006.01) |
|---|---|
| A61K 36/18 | (2006.01) |
| A61K 36/234 | (2006.01) |
| A61K 36/235 | (2006.01) |
| A61K 36/236 | (2006.01) |
| A61K 36/258 | (2006.01) |
| A61K 36/28 | (2006.01) |
| A61K 36/346 | (2006.01) |
| A61K 36/484 | (2006.01) |
| A61K 36/534 | (2006.01) |
| A61K 36/539 | (2006.01) |
| A61K 35/56 | (2006.01) |

(52) U.S. Cl.
USPC ........... 424/687; 424/547; 424/717; 424/725; 424/736; 424/741; 424/756; 424/757; 424/761; 424/764; 424/769; 424/770; 424/773; 424/775; 424/776; 424/779; 424/728

(58) Field of Classification Search
USPC ......... 424/687, 715, 717, 725, 728, 547, 736, 424/741, 756, 757, 761, 764, 769, 770, 773, 424/775, 776, 779
See application file for complete search history.

(56) References Cited

U.S. PATENT DOCUMENTS 5,411,733 A 5/1995 Hozumi et al.

FOREIGN PATENT DOCUMENTS

| JP | 1-121217 | 5/1989 |
| JP | 6-025003 | 2/1994 |
| JP | 7-215884 | 8/1995 |
| JP | 2000-044419 | 2/2000 |

OTHER PUBLICATIONS

Bagley, C.V., "Bovine respiratory disease," Animal Health Fact Sheet, Utah State University Cooperative Extension, pp. 1-4, Jul. 1997.*
MacAllister, C. et al., "Respiratory diseases in horses: what you can do to prevent them," Oklahoma Cooperative Extension Service VTMD-9120, Oklahoma State University, pp. 1-4, retrieved on Mar. 11, 2013 from the Internet:<http://pods.dasnr.okstate.edu/docushare/dsweb/Get/Document-2091/VTMD-9120web2010.pdf >.*
Fumino Sano et al., "Dobutsu ni Mochiiru 17 Shu no Kanpo Shoyaku Haigoyaku no Koshinkin Kassei ni Tsuite", Journal of Veterinary Epidemiology, 2005, vol. 9, No. 2, pp. 111 to 115, full text.
Kanpo Shoyakti 17 Shurui Haigo 'Shin Nakamori Jai San', [online] (retrieval date Apr. 3, 2008) Internet <URL.http://www.nakamori-seiyaku.co.jp/sangyo.htm> 2 pages.

* cited by examiner

*Primary Examiner* — John Pak
(74) *Attorney, Agent, or Firm* — Jordan and Hamburg LLP

(57) ABSTRACT

A method of treating a respiratory disease in an animal comprising the steps of administering to the animal an effective amount of a pharmaceutical composition comprising 1.5 parts by weight powdered fennel, 2.0 parts by weight powdered rhubarb, 1.0 part by weight powdered glycyrrhiza, 2.0 parts by weight powdered phellodendron bark, 1.0 part by weight powdered zedoary, 1.5 parts by weight powdered picrasma wood, 1.0 part by weight powdered matricaria chamomilla, 1.5 parts by weight powdered geranium herb, 1.0 part by weight powdered ginseng, 1.5 parts by weight powdered citrus unshiu peel, 1.0 part by weight powdered scutellaria root, 1.0 part by weight powdered magnolia bark, 2.0 parts by weight powdered oyster shell, 1.0 part by weight powdered cyperus rhizome, 2.0 parts by weight powdered platycodon root, 2.0 parts by weight powdered melia azedarach, 1.0 part by weight powdered cnidium rhizome, 2.0 parts by weight sodium bicarbonate and 4.0 parts by weight precipitated calcium carbonate in 30 parts by weight of the composition.

6 Claims, No Drawings

PHARMACEUTICAL COMPOSITION

The present application is a Divisional application of copending U.S. application Ser. No. 12/735,557, filed Jul. 27, 2010, which is the U.S. National Stage of International Application No. PCT/JP2008/051276, filed Jan. 29, 2008. The disclosures of these applications are incorporated herein by reference.

BACKGROUND OF THE INVENTION

The present invention relates to a pharmaceutical composition, and particularly relates to the pharmaceutical composition which is applied to cattle, horses, swine, sheep, goats, dogs, cats, chickens, domestic ducks, turkeys, wild ducks, ostriches and the like.

As diseases of domestic animals such as cattle, swine and chickens, the incidence of calf scours, swine pleural pneumonia and atrophic rhinitis, and chicken infectious bronchitis and colibacillosis are high. Antibiotics and synthetic antibacterial agents are used as therapeutic drugs for bacterial diseases among them, but resistant bacteria to these antibacterial agents have appeared, and no sufficient therapeutic effect has been obtained. In addition, public health problems have occurred because the drugs used remain in the bodies of domestic animals. Thus, preventive measures that do not depend on chemical therapy have been desired.

Vaccines have been used for some viral diseases in domestic animals and domestic fowl, but the effect of the vaccine is not sufficient as seen in an example of chicken infectious bronchitis. Thus, the disease still frequently occurs at present.

Domestic animals such as cattle, swine and chickens are often bred in a narrow feedlot in high concentrations in consideration of their early growth and breeding efficiency. Such a breeding method burdens domestic animals with great stress. As with human beings, excessive stress also brings an abnormality to the autonomic nervous system, resulting in occurrences of problems such as immune abnormality including allergic diseases, and constipation in domestic animals.

Also, constipation not only has a problem that a stool is not excreted, but also if the constipation persists, the constipation itself becomes stress to lose balance in the autonomic nervous system. As a result, a sympathetic nerve tone in increased, and an immunological capacity present in lymphocytes is reduced and disease (gastric ulcer and the like) due to an increase in active oxygen occurs in some cases.

Therapeutic drugs for constipation include magnesium sulfate, magnesium oxide and glauber's salt, but these have potential side effects, e.g., if they are taken in a large amount, symptoms of poisoning rarely occur and if they are taken in a large amount for a long period of time, hypermagnesemia occurs. Also, phenolphthalein-based large intestine stimulative purgatives include phenovalin, bisacodyl and sodium picosulfate, but they have the potential for side effects such as nausea, emesis and abdominal pain.

Also materials such as lactobacillus and dietary fibers derived from safe foods are available, but their effects cannot always be said to be sufficient, and new materials have been required.

Also, antihistamine agents, antiallergy agents and steroid agents are used in order to improve diseases such as pollen disease, bronchial asthma and atopic dermatitis due to a type I allergic reaction, but these agents are sometimes associated with side effects, e.g., a condition deterioration (rebound phenomenon) due to long term administration, somnolence due to an action upon the central nerve and an effect on the endocrine system through transdermal absorption.

Thus, for the purpose of safely improving allergic diseases without any side effects, a drug containing rosmarinic acid extracted from a Labiatae Plant as an active ingredient, although it is for human beings, is described in Patent Document 1. A perilla extract obtained by removing perillaldehyde and fractions of molecular weight of 10,000 or more from an ingredient obtained by extracting from stems and leaves of the Labiatae plant and treating it is described in Patent Document 2.

Patent Document 1: JP 1-121217-A
Patent Document 2: JP 7-215884-A

However, a drug having more effective drug efficacy than these food-borne drugs using perilla extracts has been demanded.

The present invention has been realized in light of the above points, and it is an object of the present invention to provide a pharmaceutical composition having various drug efficacies.

SUMMARY OF THE INVENTION

In order to accomplish the above object, the pharmaceutical composition of the present invention comprises 1.5 parts by weight powdered fennel, 2.0 parts by weight powdered rhubarb, 1.0 part by weight powdered glycyrrhiza, 2.0 parts by weight powdered phellodendron bark, 1.0 part by weight powdered zedoary, 1.5 parts by weight powdered picrasma wood, 1.0 part by weight powdered matricaria chamomilla, 1.5 parts by weight powdered geranium herb, 1.0 part by weight powdered ginseng, 1.5 parts by weight powdered citrus unshiu peel, 1.0 part by weight powdered scutellaria root, 1.0 part by weight powdered magnolia bark, 2.0 parts by weight powdered oyster shell, 1.0 part by weight powdered cyperus rhizome, 2.0 parts by weight powdered platycodon root, 2.0 parts by weight powdered melia azedarach, 1.0 part by weight powdered cnidium rhizome, 2.0 parts by weight sodium bicarbonate and 4.0 parts by weight precipitated calcium carbonate in 30 parts by weight of the composition.

Here, the powdered, fennel is uikyou in Japanese Pharmacopoeia, one kind of Chinese crude drugs, and has an action to discharge gas accumulated in the intestine (carminative action), an action to facilitate gastric movement and secretion of gastric juice (stomachic action), an analgesic action, an expectorant action and an improving action on apepsy.

Also, the powdered rhubarb is daiou in Japanese Pharmacopoeia, one kind of Chinese crude drugs, and has a cathartic action, an antibacterial action, a diuretic action and an anti-tumor action.

Further, the powdered glycyrrhiza is kanzou in Japanese Pharmacopoeia, one kind of Chinese crude drugs, and has an antidotal action, an antispasmodic action, a corticoid-like action, an inhibitory action on gastric acid secretion, an expectorant action, an anti-inflammatory action and an antitussive action.

Also, the powdered phellodendron bark is oubaku in Japanese Pharmacopoeia, one kind of Chinese crude drugs, and has an antibacterial action, an antimiotic action, an antiphlogistic action, a diuretic action and a stomachic action.

Also, the powdered zedoary is gajutsu in Japanese Pharmacopoeia, one kind of Chinese crude drugs, and has an absorption acceleratory action, an antitumor action, an aromatic stomachic action and an anti-salmonella enteritidis action.

Also, the powdered picrasma wood is nigaki in Japanese Pharmacopoeia, one kind of Chinese crude drugs, and has an anthelmintic action, a stomachic action and an antiprotozoal action.

Also, the powdered matricaria chamomilla is one kind of Chinese crude drugs in Japanese Pharmacopoeia, and has an analgesic action, a perspiration action, a carminative action, an antiphlogistic action, an anti-cold action, an anti-rheumatoid action, an antidiarrheal action and an anti-adenoiditis action.

Also, powdered geranium herb is one kind of Chinese crude drugs in Japanese Pharmacopoeia, and has an antidiarrheal action and a stomachic action.

Also, the powdered ginseng is ninjin in Japanese Pharmacopoeia, one kind of Chinese crude drugs, and has a stimulant action on a nerve system, a stimulant action on a pituitary-adrenal cortex system, an augmenting action on sexual functions, a cardiotonic action, a lowering action on blood sugar, an action to enhance digestion absorption and metabolism to accelerate an appetite to promote protein synthesis, an antidiuretic action, an antianaphylaxis action, an improving action on asitia, an antidiarrheal action, a fatigue recovering action, an improving action on nervous breakdown and a stomachic action.

Also, the powdered citrus unshiu peel is chinpi in Japanese Pharmacopoeia, one kind of Chinese crude drugs, and has an expectorant action, an antitussive action, a perspiration action and a stomachic action.

Also, powdered scutellaria root is ougon in Japanese Pharmacopoeia, one kind of Chinese crude drugs, and has an antipyretic action, a diuretic action, an antibacterial action, an infection prevention action against influenza (antiviral action), an antimiotic action, a sedative action, an antihypertensive effect, an improving action on the asitia, an analgesic action, an antidiarrheal action, an antiphlogistic action, an antiemetic action and a constipating action.

Also, the powdered magnolia bark is kouboku in Japanese Pharmacopoeia, one kind of Chinese crude drugs, and has an antibacterial action, an antispasmodic action, a stomachic action, an anthelmintic action, a diuretic action, an expectorant action, an antiemetic action and a constipating action.

Also, the powdered oyster shell is kaki in Japanese Pharmacopoeia, one kind of Chinese crude drugs, and has a sedative action, an analgesic action, an astringent action, an antipyretic action and a tumor resolving action.

Also, powdered cyperus rhizome is koubushi in Japanese Pharmacopoeia, one kind of Chinese crude drugs, and has an analgesic action, an antidepressant action, an analgesic action, an analgesic action, an improving action on the asitia and an antibacterial action.

Also, the powdered platycodon root is kikyou in Japanese Pharmacopoeia, one kind of Chinese crude drugs, and has an expectorant action, an antiussive action, an anti-cold action, an antimiotic action and an anti-salmonella enteritidis action.

Also, the powdered melia azedarach (kurenpi) is one kind of Chinese crude drugs, and has an anthelmintic action and an constipating action.

Also, the powdered cnidium rhizome is senkyuu in Japanese Pharmacopoeia, one kind of Chinese crude drugs, and has an antispasmodic action, a sedative action, an antihypertensive action, a vasodilating action, an antibacterial action and an antimiotic action.

Also, sodium bicarbonate is sodium bicarbonate in Japanese Pharmacopoeia, and has an antacid action on gastritis and the like, an improving action on acidosis and an acceleratory action on uric acid excretion. Also, precipitated calcium carbonate is calcium carbonate in Japanese Pharmacopoeia, and has an antacid action on gastritis and the like and an improving action on hyperphosphatemia.

Also, the pharmaceutical composition of the present invention can be used as a therapeutic drug for each of respiratory diseases, coccidiosis, dermatomycosis, cryptosporidiosis, colibacillosis and viral infectious diseases.

The pharmaceutical composition of the present invention has various drug efficacies.

DESCRIPTION OF THE PREFERRED EMBODIMENTS

The pharmaceutical composition of the present invention is one in which 17 kinds of Chinese crude drugs have been blended, and has 1.5 parts by weight powdered fennel, 2.0 parts by weight powdered rhubarb, 1.0 part by weight powdered glycyrrhiza, 2.0 parts by weight powdered phellodendron bark, 1.0 part by weight powdered zedoary, 1.5 parts by weight powdered picrasma wood, 1.0 part by weight powdered matricaria chamomilla, 1.5 parts by weight powdered geranium herb, 1.0 part by weight powdered ginseng, 1.5 parts by weight powdered citrus unshiu peel, 1.0 part by weight powdered scutellaria root, 1.0 part by weight powdered magnolia bark, 2.0 parts by weight powdered oyster shell, 1.0 part by weight powdered cyperus rhizome, 2.0 parts by weight powdered platycodon root, 2.0 parts by weight powdered melia azedarach, 1.0 part by weight powdered cnidiumn rhizome, 2.0 parts by weight sodium bicarbonate and 4.0 parts by weight precipitated calcium carbonate in 30 parts by weight of the composition.

In addition, each of 17 kinds of Chinese crude drugs is in a powder form.

Also, the pharmaceutical composition of the present invention includes various Chinese crude drugs, and thus includes various glycosides. The glycoside included in the pharmaceutical composition of the present invention includes, for example, a phenylpropanoid glycoside, a glycoside of benzyl alcohol derivative, a phenylethanoid glycoside, an anethole glycoside, a glycol glycoside, a monoterpenoid glycoside, baicalin, glycyrrhizin, a phenylpropanoid glycoside, sennoside, a flavonoid glycoside and ginsenoside.

Also, when the pharmaceutical composition of the present invention is administered to an animal, the pharmaceutical composition is kneaded with water of a small amount to form a paste, and the obtained paste is adhered on or around the mouth of the animal, or mixed with a feedstuff, or administered orally.

Also, 1 dosage of the pharmaceutical composition of the present invention varies depending on the kind and weight of the animal. The 1 dosage is described below for each animal class and each weight class.

For example, 1 dosage of the pharmaceutical composition of the present invention is 15 to 60 g for cattle weighing 300 kg or more, 7.5 to 30 g for cattle weighing 100 to 300 kg and 3.75 to 15 g for cattle weighing 100 kg or less.

Also, for example, 1 dosage of the pharmaceutical composition of the present invention is 3 to 12 g for swine weighing 100 kg or more.

Also, for example, 1 dosage of the pharmaceutical composition of the present invention is 1.5 to 6 g for sheep and a goat weighing 30 to 100 kg, 1 to 4 g for sheep and a goat weighing 10 to 30 kg and 0.6 to 2.4 g for sheep and a goat weighing 10 kg or less.

Also, for example, 1 dosage of the pharmaceutical composition of the present invention is 0.15 to 0.6 g for a cat weighing 3 kg or more, 0.075 to 0.3 g for a cat weighing 1 to 3 kg and 0.0375 to 0.15 g for a cat weighing 1 kg or less.

Also, for example, 1 dosage of the pharmaceutical composition of the present invention is 10 to 40 g for a horse weighing 300 kg or more, to 20 g for a horse weighing 100 to 300 kg and 2.5 to 10 g for a horse weighing 100 kg or less.

Also, for example, 1 dosage of the pharmaceutical composition of the present invention is 0.7 to 2.8 g for a dog weighing 20 kg or more, 0.35 to 1.4 g for a dog weighing 5 to 20 kg and 0.1.75 to 0.7 g for a dog weighing kg or less.

Also, for example, 1 dosage of the pharmaceutical composition of the present invention is 0.07 to 0.28 g for a chicken in a late chick stage, 0.035 to 0.14 g for a chicken in an intermediate chick stage and 0.0175 to 0.07 g for a chicken in a young chick stage.

The pharmaceutical composition of the present invention blends 17 kinds of Chinese crude drugs as described above, and thus, ameliorates the symptom in gastrointestinal diseases, gastrointestinal debility and asitia and ameliorates the symptom in diarrhea, gastritis, gastrointestinal ulcer, constipation and colic pain. Since further drug efficacy can be expected, the pharmaceutical composition of the present invention was used for respiratory diseases, coccidiosis, dermatomycosis, cryptosporidiosis, colibacillosis, clostridiosis and viral infectious diseases, and the presence or absence of its effect was confirmed.

(Therapeutic Effect on Respiratory Infectious Disease)

The pharmaceutical composition (30 g) of the present invention was administered twice daily to 9 growing Japanese Black Cattle aged 7 to 8 months and having respiratory symptoms, and their results were examined.

The body temperature during the first medical examination was $39.7 \pm 0.4°$ C. and the body temperature after two days was $39.3 \pm 0.4°$ C. A significant difference ($p<0.01$) was observed. The body temperature became $38.9 \pm 0.3°$ after 4 days, and the condition changed almost for the better.

The breathing rate during the first medical examination was $53.8 \pm 16.1$ times/minute, and it became $45.0 \pm 11.7$ times/minute on the next day. A significant difference ($p<0.05$) was observed.

Subsequently, a change in the body temperature 2 hours after the administration was observed in 9 Japanese Black Cattle aged 4 to 6 months. In 5 cattle to which the pharmaceutical composition of the present invention was administered according to the above example of the dosage, the body temperature was $39.6 \pm 0.6°$ C. before administration and $39.7 \pm 0.5°$ C. after administration. No difference was observed. In 4 cattle to which the pharmaceutical composition of the present invention was administered in dosage twice the aforementioned dosage, the body temperature was $39.8 \pm 0.4°$ C. before administration and lowered to $39.6 \pm 0.6°$ C. A significant difference ($p<0.05$) was observed.

(Preventive Effect on Respiratory Infectious Disease)

Tilmicosin (3000 mg) was administered once to 16 cattle aged about 10 months introduced into a fattening farm around the same time and 15 g of the pharmaceutical composition of the present invention was mixed with their feedstuff twice daily continuously for a week (test cattle group).

As controls, 3000 mg of tilmicosin alone was administered once to cattle aged about 10 months (control cattle group).

1 week after the introduction, a fever ($39.5 \pm 0.3°$ C.) was observed in 2 cattle (12.5%) and purulent nasal discharge was observed in 6 cattle (37.5%) in the test cattle group. A fever ($40.5 \pm 0.7°$ C.) was observed in 6 cattle (15.0%) and purulent nasal discharge was observed in 26 cattle (65.0%) in the control cattle group.

Also, An $\chi^2$ (chi-square) test was carried out for the number of cattle with purulent nasal discharge, but no significant difference was observed.

Therefore, the efficacy of the pharmaceutical composition of the present invention for respiratory diseases was confirmed.

(Therapeutic Effect on Coccidiosis)

The pharmaceutical composition (7.5 to 60 g) of the present invention was orally administered once or twice daily to 4 cattle with coccidiosis having bloody stools as a main symptom (1 Japanese Black Calf aged 2 months and 3 fattening Japanese Black Cattle aged 20 to 24 months) as the test cattle group. The number of coccidium oocysts (OPG) during the first medical examination was made 100%, and its change was observed. OPG during the second medical examination became 40% or less in all 4 cattle, and subsequently OPG was steadily reduced and the cattle were cured.

As the control cattle group, Ektecin solution (7.5 g/100 ml of sulfamonomethoxine and 2.5 g/100 ml of ormethoprim) which was a sulfur agent was orally administered once daily (0.15 ml/kg) to 3 cattle with coccidiosis having bloody stools as the main symptom, and their changes were observed. OPG during the second medical examination became 50% or less, and the cattle were rapidly cured.

Also, as the control cattle group, 30 g of Nutkin L (lactobacillus $4 \times 10^{78}$/g, *Bacillus subtilis* $2 \times 10^{78}$/g), which was an attenuated vaccine, was orally administered once or twice daily to 2 cattle with coccidiosis having bloody stools as the main symptom, and their changes were observed. OPG during the second medical examination was 63.5% and OPG during the third medical examination was 80.4% in 1 of the 2 cattle. In the other cattle, OPG during the second medical examination was 77% and OPG during the third medical examination was 92%. Thus, the pharmaceutical composition of the present invention was administered during the third medical examination, and OPG during the fourth medical examination was 20% or less in both the 2 cattle. They were cured during the sixth medical examination. OPG was measured using a ring method.

Therefore, the efficacy of the pharmaceutical composition of the present invention for coccidiosis was confirmed.

(Therapeutic Effect on Dermatomycosis)

An infusion of the pharmaceutical composition of the present invention and a solution obtained by mixing the pharmaceutical composition of the present invention with water was directly applied to 7 Japanese Black Calves aged 3 to 7 months with dermatomycosis. In 4 of the 7 calves, hair growth was observed within 1 month, and they were cured. Also, the remaining 3 calves were cured within 1.5 months. Loss of scales was observed within 15 days after the start of treatment in all of the calves.

Therefore, the efficacy of the pharmaceutical composition of the present invention for dermatomycosis was confirmed.

(Therapeutic Effect on Cryptosporidiosis)

The attenuated vaccine alone was administered on the date of the first medical examination and the second day to 1 of 7 cattle with cryptosporidiosis having watery diarrhea, emesis and dehydration with abdominal pain (case 1) and the pharmaceutical composition alone of the present invention mixed with the feedstuff was administered from the third day. The pharmaceutical composition alone of the present invention mixed with the feedstuff was administered to the remaining 6 cattle. Daily, 60 g of the pharmaceutical composition of the present invention was administered.

As a result, the cattle in case 1 were cured on the sixth day after the first medical examination. Among 6 cattle to which the pharmaceutical composition alone of the present invention mixed with the feedstuff had been administered, 3 were cured on the second day, two were cured on the third day and 1 was cured on the fourth day.

Therefore, the efficacy of the pharmaceutical composition of the present invention for cryptosporidiosis was confirmed.

(Therapeutic Effect on Colibacillosis)

In order to examine the drug efficacy of the pharmaceutical composition of the present invention for layers with colibacillosis, the pharmaceutical composition of the present invention in a daily amount of 3 kg per 10,000 layers was mixed with the feedstuff, which was then administered to the layers with colibacillosis for 5 days from Day 12 to Day 16. Results are shown in Tables 1 and 2.

TABLE 1

|  | Number of dead layers | Number of survival layers | Mortality rate |
|---|---|---|---|
| Day 1 | 16 | 18,845 | 0.0849% |
| Day 2 | 10 | 18,835 | 0.0531% |
| Day 3 | 24 | 18,811 | 0.1276% |
| Day 4 | 8 | 18,803 | 0.0425% |
| Day 5 | 12 | 18,791 | 0.0639% |
| Day 6 | 8 | 18,783 | 0.0426% |
| Day 7 | 11 | 18,772 | 0.0586% |
| Day 8 | 3 | 18,769 | 0.0160% |
| Day 9 | 7 | 18,762 | 0.0373% |
| Day 10 | 11 | 18,751 | 0.0587% |
| Day 11 | 10 | 18,741 | 0.0534% |
| Day 12 | 6 | 18,735 | 0.0320% |
| Day 13 | 9 | 18,726 | 0.0481% |
| Day 14 | 6 | 18,720 | 0.0321% |
| Day 15 | 9 | 18,711 | 0.0481% |
| Day 16 | 11 | 18,700 | 0.0588% |
| Day 17 | 10 | 18,690 | 0.0535% |
| Day 18 | 11 | 18,679 | 0.0589% |
| Day 19 | 6 | 18,673 | 0.0321% |
| Day 20 | 10 | 18,663 | 0.0536% |

TABLE 2

|  | Number of dead layers | Number of survival layers | Mortality rate |
|---|---|---|---|
| Day 21 | 6 | 18,657 | 0.0322% |
| Day 22 | 8 | 18,649 | 0.0429% |
| Day 23 | 6 | 18,643 | 0.0322% |
| Day 24 | 8 | 18,635 | 0.0429% |
| Day 25 | 6 | 18,629 | 0.0322% |
| Day 26 | 5 | 18,624 | 0.0268% |
| Day 27 | 8 | 18,616 | 0.0430% |
| Day 28 | 12 | 18,604 | 0.0645% |
| Day 29 | 4 | 18,600 | 0.0215% |
| Day 30 | 7 | 18,593 | 0.0376% |
| Day 31 | 8 | 18,585 | 0.0430% |
| Day 32 | 4 | 18,581 | 0.0215% |
| Day 33 | 8 | 18,573 | 0.0431% |
| Day 34 | 5 | 18,568 | 0.0269% |
| Day 35 | 6 | 18,562 | 0.0323% |
| Day 36 | 5 | 18,557 | 0.0269% |
| Day 37 | 5 | 18,552 | 0.0270% |
| Day 38 | 4 | 18,548 | 0.0216% |
| Day 39 | 3 | 18,545 | 0.0162% |
| Day 40 | 3 | 18,542 | 0.0162% |
| Day 41 | 7 | 18,535 | 0.0378% |

As is shown in Tables 1 and 2, the number of dead layers for days from Day 12 to Day 1.6 when the pharmaceutical composition of the present invention had been administered and the number of dead layers after the administration were lower in average than the number of dead layers before the administration.

Therefore, the efficacy of the pharmaceutical composition of the present invention for colibacillosis was confirmed.

(Therapeutic Effect on Clostridiosis)

In order to examine the drug efficacy of the pharmaceutical composition of the present invention for layers with clostridiosis, the pharmaceutical composition of the present invention in a daily amount of 0.28 g per layer was mixed with the feedstuff, which was then administered to the layers which had developed clostridiosis on Day 13 for 4 days from Day 20 to Day 23. For 1 day on Day 28, 10 kg of the pharmaceutical composition of the present invention was mixed with the feedstuff, which was then also administered to the layers. The results are shown in Tables 3 and 4.

TABLE 3

|  | Number of dead layers | Number of survival layers |
|---|---|---|
| Day 1 | 4 | 47,896 |
| Day 2 | 8 | 47,888 |
| Day 3 | 7 | 47,881 |
| Day 4 | 6 | 47,875 |
| Day 5 | 12 | 47,863 |
| Day 6 | 12 | 47,851 |
| Day 7 | 7 | 47,844 |
| Day 8 | 8 | 47,836 |
| Day 9 | 7 | 47,829 |
| Day 10 | 7 | 47,822 |
| Day 11 | 12 | 47,810 |
| Day 12 | 90 | 47,790 |
| Day 13 | 30 | 47,760 |
| Day 14 | 30 | 47,730 |
| Day 15 | 25 | 47,705 |
| Day 16 | 18 | 47,687 |
| Day 17 | 27 | 47,660 |
| Day 18 | 25 | 47,635 |
| Day 19 | 25 | 47,610 |
| Day 20 | 20 | 47,590 |

TABLE 4

|  | Number of dead layers | Number of survival layers |
|---|---|---|
| Day 21 | 16 | 47,574 |
| Day 22 | 24 | 47,550 |
| Day 23 | 20 | 47,530 |
| Day 24 | 15 | 47,515 |
| Day 25 | 14 | 47,501 |
| Day 26 | 18 | 47,483 |
| Day 27 | 10 | 47,473 |
| Day 28 | 17 | 47,456 |
| Day 29 | 13 | 47,443 |
| Day 30 | 4 | 47,439 |
| Day 31 | 3 | 47,436 |
| Day 32 | 12 | 47,424 |
| Day 33 | 10 | 47,414 |
| Day 34 | 8 | 47,406 |
| Day 35 | 6 | 47,400 |

As is shown in Tables 3 and 4, the number of dead layers with clostridiosis was 20 or more except Day 16, but the number of dead layers became less than 20 from Day 24 after administering the pharmaceutical composition of the present invention for 4 days, and further the number of dead layers did not exceed 15 after administering the pharmaceutical composition of the present invention again on Day 28.

Therefore, the efficacy of the pharmaceutical composition of the present invention for clostridiosis was confirmed.

(Therapeutic Effect on Viral Infectious Disease)

The pharmaceutical composition (60 g) of the present invention mixed with water was administered daily to 7 cattle exhibiting the symptom of infectious diarrhea due to the infection with corona virus.

As a result, among the 7 cattle, 3 were given the pharmaceutical composition of the present invention for 2 days and were cured 4 days after the first medical examination, the other 3 were given it for 3 days and were cured 5 days after the first medical examination, and the remaining 1 was given it for 4 days and was cured 9 days after.

Therefore, the efficacy of the pharmaceutical composition of the present invention for the viral infectious disease was confirmed.

As described above, the pharmaceutical composition of the present invention blends 17 kinds of Chinese crude drugs, and thus has the therapeutic effects on the respiratory disease, coccidiosis, dermatomycosis, cryptosporidiosis, colibacillosis, clostridiosis and the viral infectious disease, in addition to the ameliorating effects on the symptoms in gastrointestinal diseases, the gastrointestinal debility and the asitia as well as the ameliorating effects on the symptoms in diarrhea, gastritis, gastrointestinal ulcer, constipation and colic pain.

The invention claimed is:

1. A method of treating a respiratory infectious disease in an animal other than humans comprising the steps of administering to the animal an effective amount of a pharmaceutical composition comprising:
   1.5 parts by weight powdered fennel;
   2.0 parts by weight powdered rhubarb;
   1.0 part by weight powdered glycyrrhiza;
   2.0 parts by weight powdered phellodendron bark;
   1.0 part by weight powdered zedoary;
   1.5 parts by weight powdered picrasma wood;
   1.0 part by weight powdered matricaria chamomilla;
   1.5 parts by weight powdered geranium herb;
   1.0 part by weight powdered ginseng;
   1.5 parts by weight powdered citrus unshiu peel;
   1.0 part by weight powdered scutellaria root;
   1.0 part by weight powdered magnolia bark;
   2.0 parts by weight powdered oyster shell;
   1.0 part by weight powdered cyperus rhizome;
   2.0 parts by weight powdered platycodon root;
   2.0 parts by weight powdered melia azedarach;
   1.0 part by weight powdered cnidium rhizome;
   2.0 parts by weight sodium bicarbonate; and
   4.0 parts by weight precipitated calcium carbonate in 30 parts by weight of the composition.

2. The method of claim 1 wherein the pharmaceutical composition is administered orally to the animal.

3. The method of claim 1 wherein the animal is a domesticated animal.

4. The method of claim 1 wherein the animal is a non-domesticated animal.

5. The method of claim 1 wherein the animal is selected from the group of cattle, horses, swine, sheep, goats, dogs, cats, chickens, ducks, turkeys, and ostriches.

6. The method of claim 1 wherein the animal is a cattle animal.

* * * * *